US009655501B2

(12) United States Patent
Kaufman

(10) Patent No.: US 9,655,501 B2
(45) Date of Patent: May 23, 2017

(54) SIDE-SCAN INFRARED IMAGING DEVICES

(71) Applicant: Public Service Solutions, Inc., Fresh Meadows, NY (US)

(72) Inventor: Peter N. Kaufman, Fresh Meadows, NY (US)

(73) Assignee: Digital Direct IR, Inc., Fresh Meadows, NY (US)

( * ) Notice: Subject to any disclaimer, the term of this patent is extended or adjusted under 35 U.S.C. 154(b) by 233 days.

(21) Appl. No.: 14/315,294

(22) Filed: Jun. 25, 2014

(65) Prior Publication Data

US 2015/0057548 A1 Feb. 26, 2015

Related U.S. Application Data

(60) Provisional application No. 61/839,348, filed on Jun. 25, 2013.

(51) Int. Cl.
| | |
|---|---|
| *A61B 5/00* | (2006.01) |
| *A61B 1/04* | (2006.01) |
| *G01J 5/50* | (2006.01) |
| *G01J 5/04* | (2006.01) |
| *G01J 5/02* | (2006.01) |
| *G01J 5/08* | (2006.01) |
| *A61B 1/00* | (2006.01) |
| *A61B 1/05* | (2006.01) |

(Continued)

(52) U.S. Cl.
CPC .......... *A61B 1/041* (2013.01); *A61B 1/00096* (2013.01); *A61B 1/05* (2013.01); *A61B 1/0638* (2013.01); *A61B 5/0075* (2013.01); *G01J 5/0215* (2013.01); *G01J 5/041* (2013.01); *G01J 5/0893* (2013.01); *G01J 5/505* (2013.01); *G01J 2005/0077* (2013.01)

(58) Field of Classification Search
CPC ....... A61B 1/00096; A61B 1/041; A61B 1/05; A61B 1/0638; A61B 5/0075; G01J 2005/0077; G01J 5/0215; G01J 5/041; G01J 5/0893; G01J 5/505
See application file for complete search history.

(56) References Cited

U.S. PATENT DOCUMENTS

| | | |
|---|---|---|
| 5,469,979 A | 11/1995 | Chiou |
| 6,107,618 A | 8/2000 | Fossum et al. |
| (Continued) | | |

FOREIGN PATENT DOCUMENTS

| | | |
|---|---|---|
| WO | 2009/102445 | 8/2009 |
| WO | 2013/165689 | 11/2013 |

OTHER PUBLICATIONS

International Search Report and Written Opinion of the International Searching Authority for Counterpart PCT Application, PCT/US2014/044200, dated Oct. 30, 2014.

(Continued)

*Primary Examiner* — Ruth S Smith

(57) ABSTRACT

Infrared imaging devices are provided which are configured to implement side-scan infrared imaging for, e.g., medical applications. For example, an imaging device includes a ring-shaped detector element comprising a circular array of infrared detectors configured to detect thermal infrared radiation, and a focusing element configured to focus incident infrared radiation towards the circular array of infrared detectors. The imaging device can be an ingestible imaging device (e.g., swallowable camera) or the imaging device can be implemented as part of an endoscope device, for example.

10 Claims, 9 Drawing Sheets

(51) Int. Cl.
    *A61B 1/06*     (2006.01)
    *G01J 5/00*     (2006.01)

(56) References Cited

U.S. PATENT DOCUMENTS

| | | |
|---|---|---|
| 6,652,452 B1 | 11/2003 | Seifert et al. |
| 7,433,031 B2 | 10/2008 | Xu et al. |
| 7,465,271 B2 | 12/2008 | Kanazawa |
| 7,530,948 B2 | 5/2009 | Seibel et al. |
| 7,619,754 B2 | 11/2009 | Riel et al. |
| 7,813,538 B2 | 10/2010 | Carroll et al. |
| 7,998,059 B2 | 8/2011 | Fujimori |
| 8,382,662 B2 | 2/2013 | Soper et al. |
| 8,405,711 B2 | 3/2013 | Wang et al. |
| 8,405,832 B2 | 3/2013 | Schmaelzle et al. |
| 8,414,479 B2 | 4/2013 | Shi et al. |
| 8,466,406 B2 | 6/2013 | Hvass et al. |
| 2002/0109774 A1 | 8/2002 | Meron et al. |
| 2004/0254424 A1 | 12/2004 | Simkulet et al. |
| 2005/0004474 A1 | 1/2005 | Iddan |
| 2005/0046944 A1 | 3/2005 | Shenderova et al. |
| 2005/0088515 A1 | 4/2005 | Geng |
| 2005/0183733 A1 | 8/2005 | Kawano et al. |
| 2006/0004255 A1 | 1/2006 | Iddan et al. |
| 2006/0132780 A1 | 6/2006 | Holland et al. |
| 2009/0318761 A1 | 12/2009 | Rabinovitz |
| 2010/0249570 A1 | 9/2010 | Carson et al. |
| 2011/0112407 A1 | 5/2011 | Wood et al. |
| 2012/0105574 A1 | 5/2012 | Baker et al. |

OTHER PUBLICATIONS

Supplementary European Search Report for Counterpart European Patent Application No. EP14818019.3, dated Mar. 16, 2017 (7 pages).

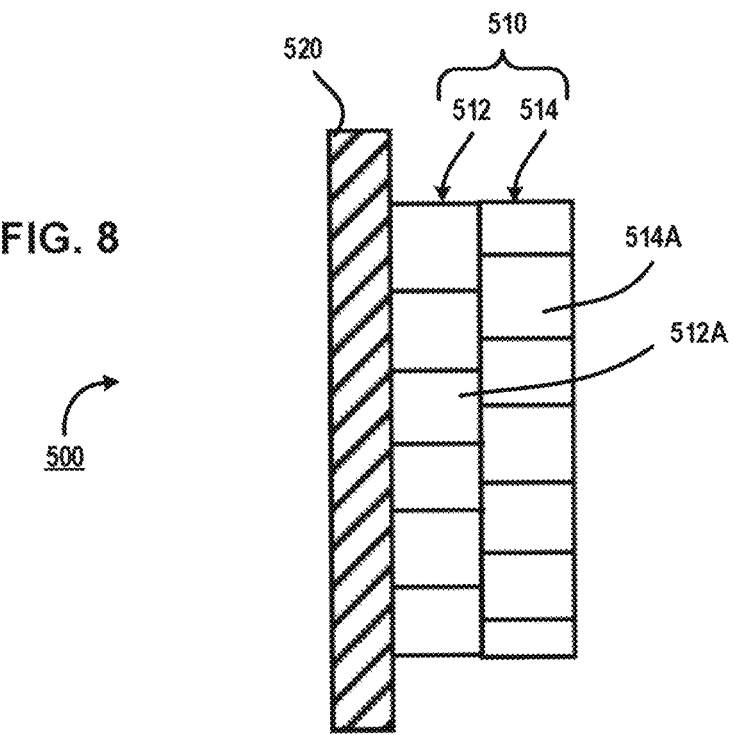
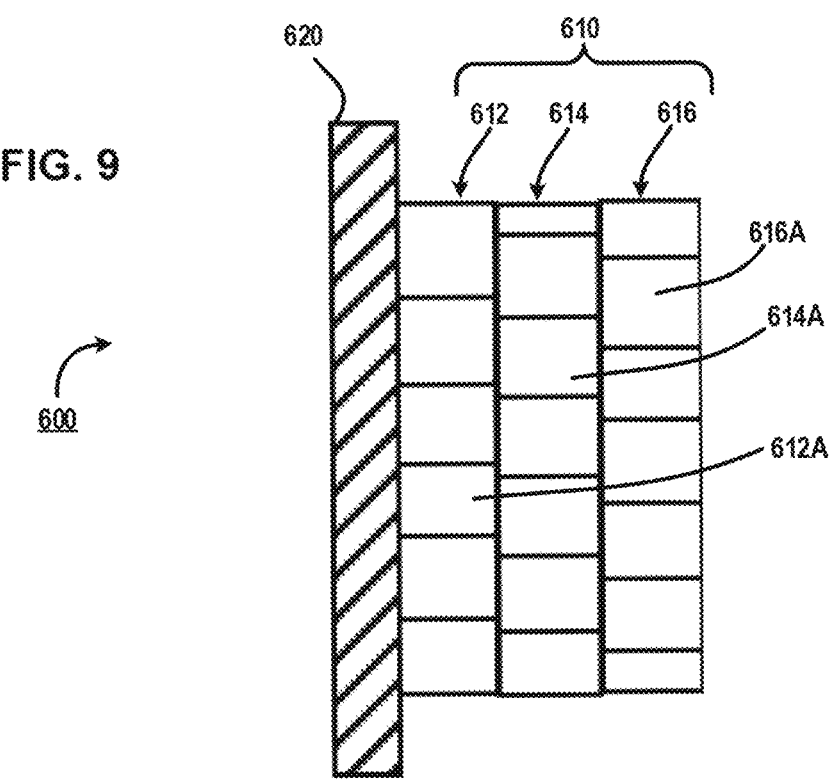

SIDE-SCAN INFRARED IMAGING DEVICES

CROSS-REFERENCE TO RELATED APPLICATION

This application claims priority to U.S. Provisional Patent Application Ser. No. 61/839,348, filed on Jun. 25, 2013, the disclosure of which is incorporated herein by reference.

TECHNICAL FIELD

The field generally relates to infrared imaging and, in particular, to medical imaging devices and methods that utilize infrared imaging.

BACKGROUND

In general, ingestible cameras (or "swallowable pill" cameras) are medical imaging devices that can be used to acquire high-resolution images within all portions of the gastrointestinal (GI) tract of an individual from mouth to anus. In general, conventional ingestible cameras are configured for imaging at wavelengths within the portion of the electromagnetic spectrum from visible to Near-Infrared (Near-IR) (about 400 nm to about 900 nm). These conventional ingestible cameras require an internal source of light to illuminate the interior lumen region of the GI tract. In some conventional ingestible pill designs, light emitting diodes (or other light sources) are used to provide the illumination that is needed for the imager detectors to acquire an image. In other words, conventional ingestible cameras utilize imaging schemes based on reflective light, wherein an external light source must shine light on a surface of the tissue of the GI tract to be imaged, and wherein an image is captured by detecting light that is reflected off the tissue surface being imaged. While these conventional ingestible cameras that use reflective light are sufficient to capture images of certain conditions (e.g., polyps on inner colon wall) that are exposed on the tissue surface of the GI tract, such cameras cannot be used to capture images or otherwise detect conditions that may exist within the GI tract tissue below the surface of the tissue.

SUMMARY

Embodiments of the invention generally include infrared imaging devices that are configured for side-scan infrared imaging for, e.g., medical applications. For example, in one embodiment of the invention, an imaging device includes a ring-shaped detector element comprising a circular array of infrared detectors configured to detect thermal infrared radiation, and a focusing element configured to focus incident infrared radiation towards the circular array of infrared detectors.

In another embodiment, the focusing element comprises a ring shaped focusing element that is disposed over the ring-shaped detector array. The ring-shaped focusing element comprises a plurality of pinholes to focus incident infrared energy towards the infrared detectors. In one embodiment, the ring-shaped focusing element includes a plurality of pinholes formed therein, wherein each infrared detector is aligned to only one pinhole. In another embodiment, the ring-shaped focusing element includes a plurality of pinholes formed therein, wherein each infrared detector is aligned to two or more of the plurality of pinholes.

In one embodiment of the invention, the imaging device is implemented as an ingestible imaging device. In another embodiment, the imaging device is implemented as part of an endoscope device.

These and other embodiments of the invention will be described or become apparent from the following detailed description of embodiments, which is to be read in conjunction with the accompanying drawings.

DESCRIPTION OF THE FIGURES

FIG. 8 is a schematic side view of a thermal IR ring-array imager according to another embodiment of the invention.

FIG. 9 is a schematic side view of a thermal IR ring-array imager according to another embodiment of the invention.

WRITTEN DESCRIPTION

Figure 1:
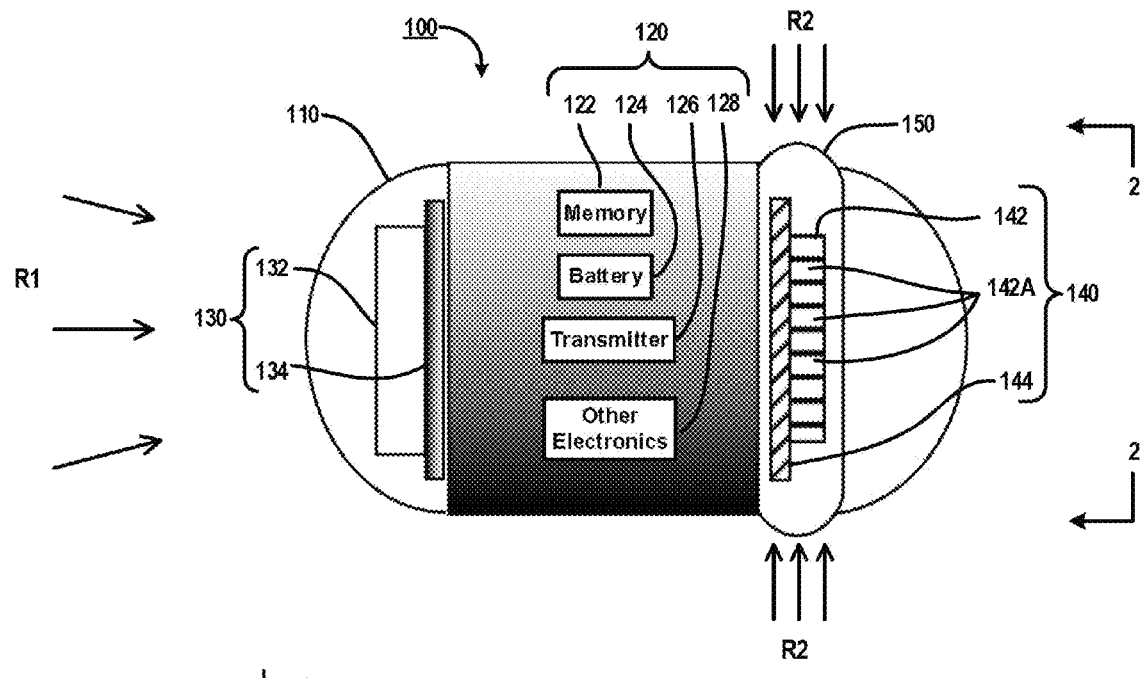
FIG. 1 schematically illustrates an ingestible imaging device according to an embodiment of the invention.

FIG. 1 is a schematic illustration of an ingestible imaging device according to an embodiment of the invention. In particular, FIG. 1 illustrates an ingestible imaging device 100 comprising a pill-shaped housing 110. The ingestible imaging device 100 further comprises electronic components 120, a visible light camera 130, and a thermal infrared ring-array imager 140, which are contained within the pill-shaped housing 110. The ingestible imaging device 100 further comprises a lens element 150 that is integrally formed as part of the pill-shaped housing 110. In one embodiment of the invention, the ingestible imaging device 100 is configured for use as medical imaging device in the form of a "swallowable pill" that can acquire high-resolution images of an individual's GI tract in multiple electromagnetic spectrums.

For instance, in one embodiment of the invention, the visible light camera 130 is configured for imaging at wavelengths within the portion of the electromagnetic spectrum from visible to Near-IR (about 400 nm to about 900 nm). The visible light camera 130 comprises various camera components 132 (e.g., optical lens, imager, etc.) mounted on a circuit board 134. In one embodiment, the camera components 132 include a 2-D focal plane array that is positioned perpendicular to a direction (denoted by line "L") of a longitudinal axis of the pill-shaped housing 110 so as to acquire "forward looking" images in the visible and Near-IR spectrums (which are reflective spectrums).

In other words, the visible light camera 130 is configured to capture images based on incident radiation (denoted by arrows labeled R1) that is essentially parallel to the longitudinal direction "L" of the pill-shaped housing 110. For a swallowable camera application, the visible light camera 130 can be made small enough to fit into a pill-shaped housing that is approximately ½ inch in diameter because at the visible and Near-IR wavelengths, the 2-D focal plane array can be made ⅓ inch or less along its diagonal.

Figure 2:
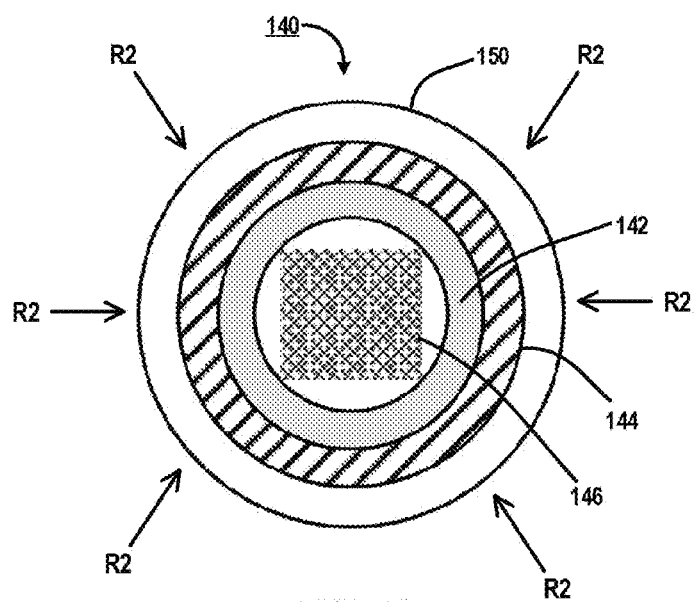
FIG. 2 is a schematic front view of the ingestible imaging device along line 2-2 in FIG. 1.
Figure 3A:
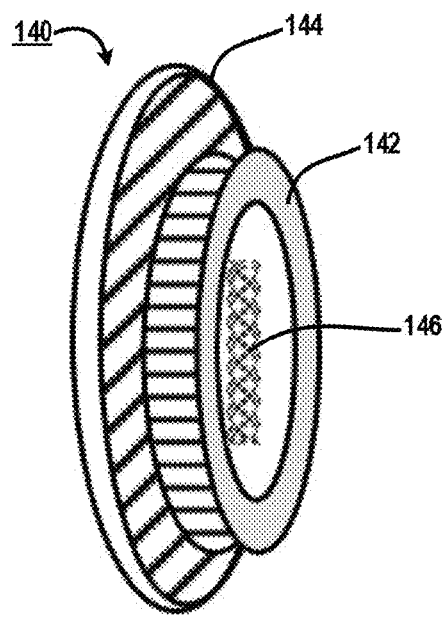
FIG. 3A is a schematic perspective view of a thermal IR ring-array imager according to an embodiment of the invention.
Figure 3B:
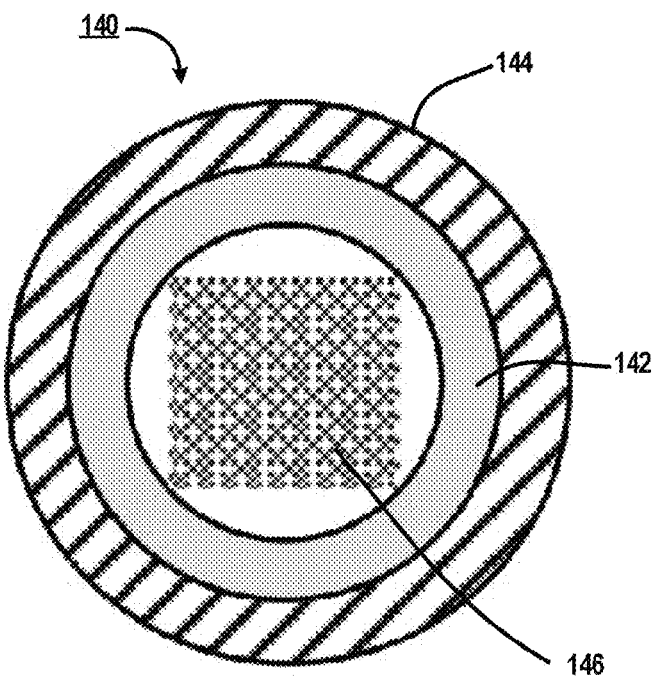
FIG. 3B is a front schematic view of the thermal IR ring-array imager of FIG. 3A, according to an embodiment of the invention.

In one embodiment of the invention, the thermal infrared ring-array imager 140 is configured for imaging at wavelengths within the thermal infrared portion of the electromagnetic spectrum from Mid-IR to Far-IR (about 2 micron to 15 microns). Further details of the thermal IR ring-array imager 140 are shown in FIGS. 2, 3A, and 3B. In particular, FIG. 2 is a schematic front view of the ingestible imaging device 100 along line 2-2 in FIG. 1. In addition, FIG. 3A is a schematic perspective view of the thermal IR ring-array imager 140, and FIG. 3B is a front schematic view of the thermal IR ring-array imager 140, according to an embodiment of the invention.

As collectively shown in FIGS. 1, 2, 3A and 3B, the thermal IR ring-array imager 140 comprises a ring-shaped detector element 142 that is formed on a substrate 144. The ring-shaped detector element 142 comprises a circular array of infrared detectors 142A (or infrared pixels) formed around an outer perimeter surface of the ring-shaped detector element 142, which enables thermal IR side-scan imaging. The thermal IR ring-array imager 140 further comprises detector circuitry 146 which is formed on the substrate 144 and electrically connected to the circular array of infrared detectors 142A. As shown in FIGS. 1 and 2, the lens element 150 is configured to focus incident IR radiation (denoted by arrows labeled R2), which is directed at the side of the pill-shaped housing 110, towards the infrared detectors 142A of the ring-shaped detector element 142. In this configuration, the thermal IR ring-array imager 140 is configured to capture images by detecting incident thermal IR radiation R2 that is directed towards the sides of the pill-shaped housing 110 in proximity to the lens element 150.

While the visible light camera 130 can only be used to capture images of conditions that may exist on the tissue surface of the GI tract, the thermal IR ring-array imager 140 can be used to capture images of conditions that may exist below the tissue surface of the GI tract, for example, 0.5 mm to 4 mm below the surface of the tissue of the GI tract. Indeed, imaging below the tissue surface can be performed using emissive radiation, which is the thermal infrared portion of the electromagnetic spectrum known as heat (2 μm to 15 μm). All physical matter emits what are referred to as "emissive photons" in the infrared portion of the electromagnetic spectrum. In addition, when viewing the spectrum that is emitted from living tissue, we see emissive photons, as well as heat that is created by biological activity of living cells. This emissive IR heat can propagate through a certain thickness of tissue of the wall of the GI tract. The magnitude of the emissive IR heat will vary based on the density of the underlying cells and the type of biological activity that the tissue performs. By filtering the IR thermal view to either 4μ or 11μ, we can isolate and view tissue of different density and heat emissivity, and thereby acquire useful data about potential abnormal conditions (e.g., tumor, cyst, granuloma, abnormal circulatory vessel, etc.) that may exist in early stages below the surface of the tissue of the GI tract, and which may not be visibly exposed on interior surface of the GI tract until some later time in the future as the abnormalities grow and acquire more cellular activity. Advantageously, thermal IR side-scan imaging devices and techniques as described herein allow for early detection of such abnormal conditions that exist below the surface of the GI tract tissue, for example.

The use and implementation of thermal IR imagers and associated optics in an ingestible imaging device is not trivial. For example, while a visible light focal plane array imager can be made small enough to fit within the pill-shaped housing 110 as noted above, the wavelength of thermal IR is much greater than that of visible light, thereby requiring the sizes of the pixels for IR detection to be much larger. This limitation prohibits the use of a 2D focal plane array for IR imaging because a thermal IR focal plane array would need to be 1¾ inches along the diagonal, which would require the pill-shaped housing 110 to be about 2 inches in diameter. This is problematic in that a person could not easily swallow something that large and the danger of obstruction or damage to the GI tract is a serious possibility. Embodiments of the invention provide an alternative side-scanning thermal IR imager configuration that is suitable for swallowable pill applications.

In one embodiment of the invention, a thermal IR ring-array imager can be implemented using the structures and method disclosed in commonly owned U.S. patent application Ser. No. 13/588,441, entitled "Passive Detectors For Imaging Systems," filed on 17 Aug. 2012, now U.S. Pat. No. 9,012,845, the disclosure of which is fully incorporated herein by reference. In U.S. patent application Ser. No. 13/588,441, various passive CTE (coefficient of thermal expansion) thermal IR detector designs are described. For example, in one embodiment, a thermal IR detector includes substrate and a resonator member having a frequency or period of oscillation and disposed on the substrate. The resonator member is a piezoelectric resonator member. A passive detector structure is also disposed on the substrate. The passive detector structure includes an unpowered detector member that is mechanically distorted in response to photon exposure to apply a mechanical force to the resonator member and change the frequency or period of oscillation of the resonator member in response to the mechanical force. A digital circuit is coupled to the resonator member, and configured to determine the frequency or period of oscillation of the resonator member, which changes due to the mechanical force exerted on the resonator member by the passive detector structure. The digital circuitry is further configured to determine an amount of incident photonic energy absorbed by the unpowered detector member based on the determined frequency. A passive CTE detector design is particularly useful for implementing thermal IR side-scan imaging structures described herein because of simplicity of the configuration, a small number of component parts of the detector, and the use of a well-known MEMS manufacturing process to construct the imagers.

In one embodiment of the invention, the substrate 144 may be formed using any suitable material such as semiconductor material (e.g., silicon), glass, ceramic, etc. The pixel circuitry 146 can be fabricated using standard CMOS semiconductor fabrication techniques or thin-film device fabrication techniques, for example. The ring-shaped detector element 142 can be fabricated using standard MEMS manufacturing technologies to build the circular array of infrared detectors 142A and the interconnect structures needed to electrically connect the infrared detectors 142A to the pixel circuitry 146.

In the embodiment of FIG. 1, the electronic components 120 include components such as a memory device 122, a battery 124, a transmitter 126 and other electronics that are typically utilized in swallowable pill cameras to provide the necessary functionalities. The memory 122 can be utilized to storage image data that is captured, and subsequently downloaded to a computing system having software that is capable of processing and rendering the image data. The transmitter 126 can be included to transmit image data that is captured by the imaging device 100 to a remote device, wherein the image data is stored and/or processed.

With regard to the focusing optics for the thermal IR ring-array imager 140, the lens element 150 shown in FIG. 1, for example, provides a cost effective lens solution, as the lens element 150 can be molded using the same plastic material that is used to form the pill-shaped housing 110. Indeed, with regard to focusing ability, the lens element 150 made from molded plastic can provide effective focusing for "micro" level distances of 500 µm to 5 mm, for example, that are expected between the thermal IR detectors and GI tract tissue (including the distance related to the emissive thickness of the tissue) when conducting side-scan IR imaging within close proximity to the tissue surface of the GI tract.

Moreover, although plastic material may result in significant photonic energy losses and consequently, a loss of sensitivity of the thermal IR detectors, this loss is acceptable in the given application as there would still remain a substantial amount of IR radiation energy for effective imaging due to the close proximity between the thermal IR detectors and the source of IR radiation (i.e., the tissue of the GI tract). The thermal IR ring-array imager 140 can be properly aligned to the lens element 150 when mounting the thermal IR ring-array imager 140 within the pill-shaped housing 110.

Figure 4:
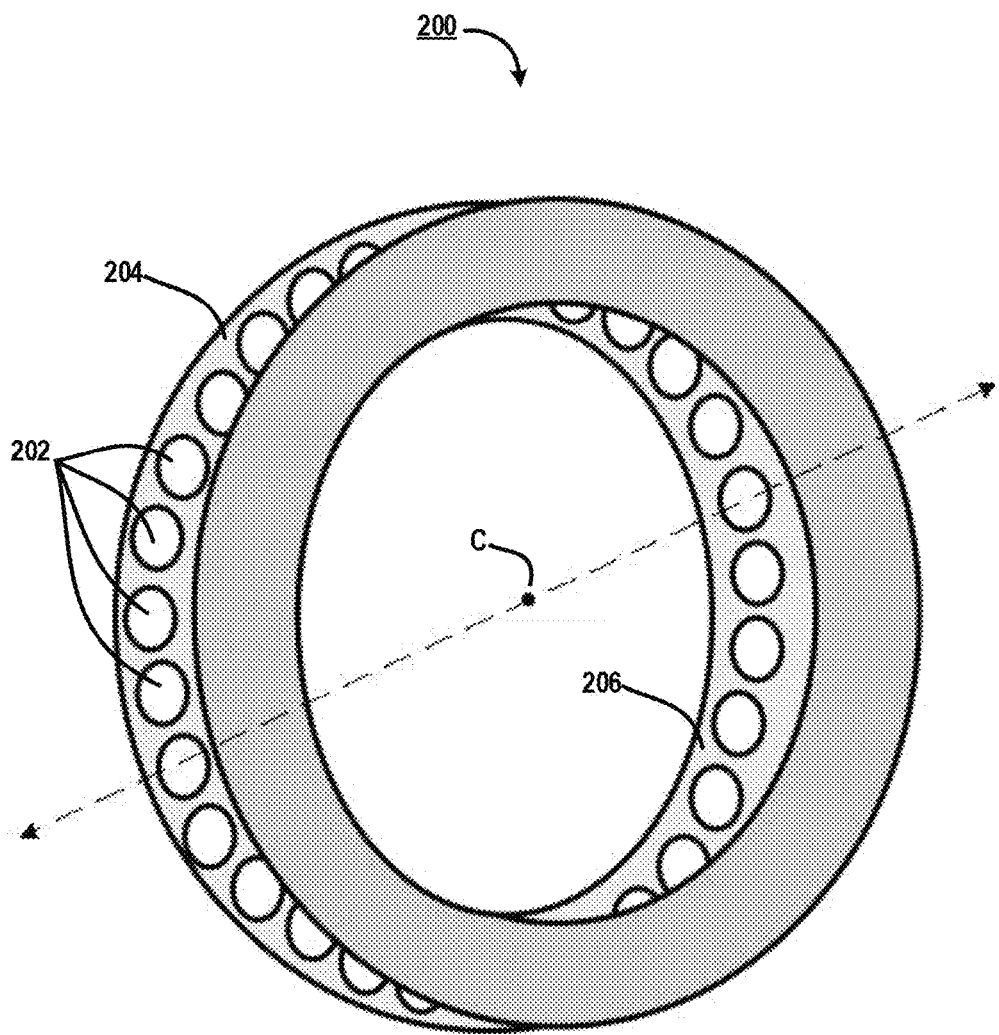
FIG. 4 is a schematic perspective view of a ring-shaped focusing element, according to an embodiment of the invention.

In another embodiment of the invention, the optics for the thermal IR ring-array imager 140 can be implemented using a ring-shaped focusing element with pinholes, which is disposed over the ring-shaped detector element 142. For example, FIG. 4 is a schematic perspective view of a ring-shaped focusing element 200 according to an embodiment of the invention, which can be used in place of the lens element 150 shown in FIG. 1 to focus incident IR radiation towards the infrared detectors 142A of the ring-shaped detector element 142. In particular, as depicted in FIG. 4, the ring-shaped focusing element 200 comprises a plurality of through-holes 202 (or alternatively, "pinholes") that extend through a thickness of the ring-shaped focusing element 200 from an outer surface 204 to an inner surface 206 thereof. Each through-hole 202 extends in radial alignment to a center point C of the ring-shaped focusing element 200, as indicated by the dashed arrow shown in FIG. 4. The ring-shaped focusing element 200 may be formed of any suitable material such as plastic, metal or ceramic, wherein the through-holes 202 are formed by using standard drilling techniques such as, e.g., mechanical drilling, etching, laser cut, etc.

Figure 5:
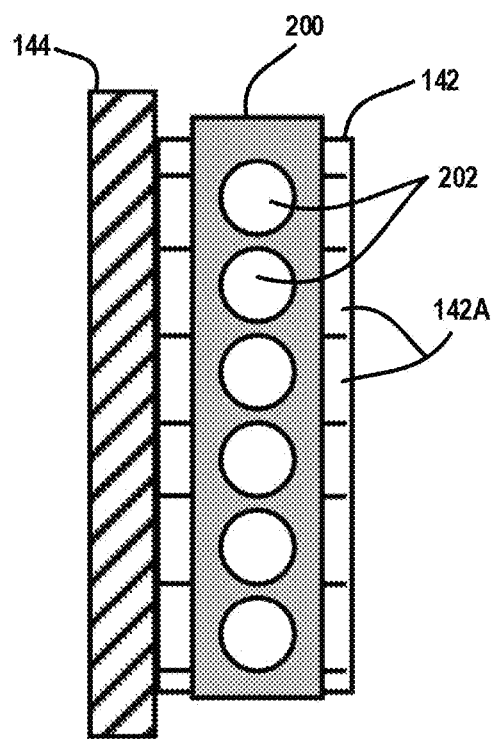
FIG. 5 schematically illustrates the use of the ring-shaped focusing element of FIG. 4 with a thermal IR ring-array imager, according to an embodiment of the invention.

FIG. 5 schematically illustrates the use of the ring-shaped focusing element 200 of FIG. 4 with a thermal IR ring-array imager, according to an embodiment of the invention. As shown in FIG. 5, the ring-shaped focusing element 200 is positioned over the ring-shaped detector element 142 such that each through-hole 202 is aligned to a center region of a given one of the infrared detectors 142A of the ring-shaped detector element 142. As compared to use of the lens element 150 shown in FIG. 1, the ring-shaped focusing element 200 implements a pin-hole camera based approach for focusing thermal IR radiation towards the infrared detectors 142A. This pinhole focusing design enables IR imaging with a larger depth of field and minimizes the attenuation of incident IR energy that can be expected from the lens element 150 made of a plastic. The pinhole concept is suitable in the given application as the small aperture of the through-holes 202 only allows photonic energy traveling perpendicular to the detector to pass through the through-holes 202 (IR radiation that is in focus), and otherwise blocks IR energy that has angular vectors (IR radiation that is not in focus).

In the embodiment shown in FIG. 5, as noted above, the ring-shaped focusing element 200 must be positioned such that each through-hole 202 is substantially aligned to a central region of a given one of the infrared detectors 142A of the ring-shaped detector element 142. In another embodiment of the invention, a ring-shaped focusing element can be fabricated having a larger amount of smaller diameter through-holes such that multiple smaller sized through-holes are aligned to each one of the infrared detectors 142A of the ring-shaped detector element 142.

Figure 6:
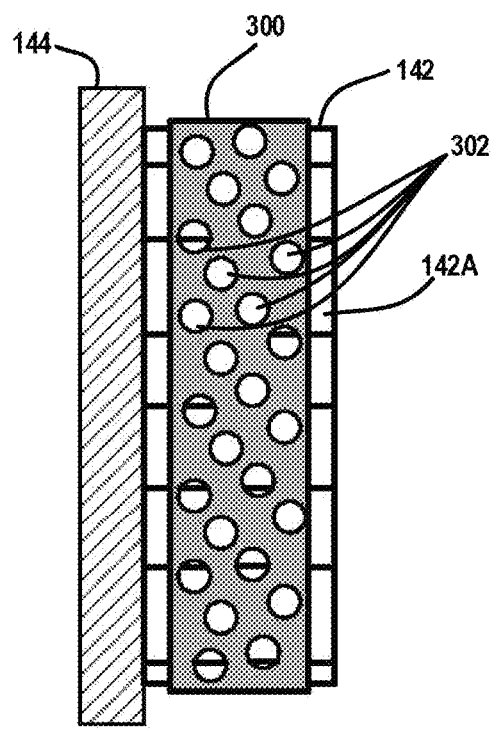
FIG. 6 illustrates a ring-shaped focusing element according to another embodiment of the invention.

For example, FIG. 6 illustrates a ring-shaped focusing element 300 according to another embodiment of the invention. Similar to the embodiment of FIG. 5, the ring-shaped focusing element 300 is disposed around the ring-shaped detector element 142. However, in the exemplary embodiment of FIG. 6, two or more through-holes 302 of the ring-shaped focusing element 300 are aligned to the same infrared detector 142A. This embodiment of the ring-shaped focusing element 300 can be more easily aligned with the ring-shaped detector element 142 because any individual infrared detector 142A would receive focused IR radiation from a more than one through-hole 302. In this regard, as compared to the embodiment of FIG. 5, using multiple pinholes per infrared detector reduces the critical nature of the alignment while still allowing sufficient focused IR energy to reach the infrared detectors. The size and number of through-holes in each of the embodiments of the ring-shaped focusing elements 200 and 300 are wavelength dependent and based on the pixel detector size.

Figure 7:
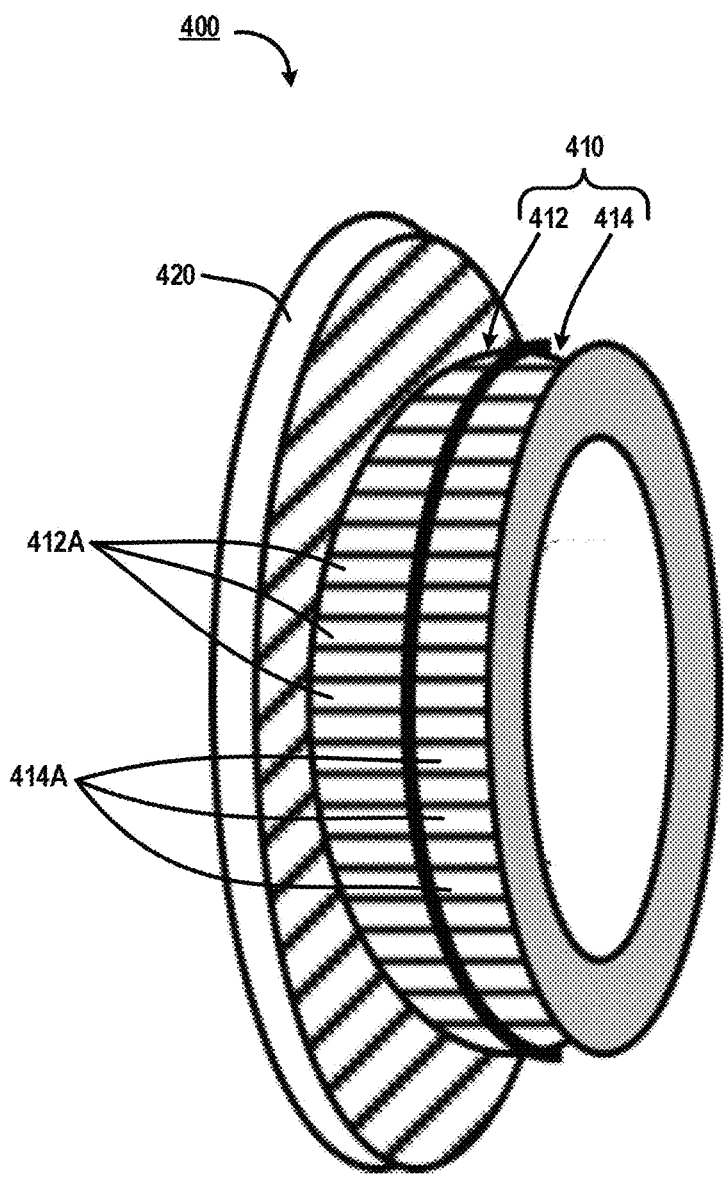
FIG. 7 is a schematic perspective view of a thermal IR ring-array imager according to another embodiment of the invention.

FIG. 7 is a schematic perspective view of a thermal IR ring-array imager according to another embodiment of the invention. In particular, FIG. 7 schematically depicts a thermal IR ring-array imager 400 comprising a ring-shaped detector element 410 that is formed on a substrate 420. The ring-shaped detector element 410 comprises a first circular array of infrared detectors 412 and a second circular array of infrared detectors 414, wherein the first and second circular arrays 412 and 414 comprise a plurality of infrared detectors 412A and 414A, respectively. The thermal IR ring-array imager 400 with two circular arrays of infrared detectors 412 and 414 provides increased resolution for IR imaging, as compared to a thermal IR ring-array imager having a single circular array of infrared detectors. In one embodiment of the invention, the infrared detectors 412A and 414A of the ring-shaped detector element 410 are aligned to each other in a direction perpendicular to the plane of the substrate 420. A ring-shaped focusing element can be implemented with the thermal IR ring-array imager 400 of FIG. 7 using similar techniques discussed above with reference to FIGS. 4, 5 and 6.

FIG. 8 is a schematic side view of a thermal IR ring-array imager according to another embodiment of the invention.

In particular, FIG. 8 schematically depicts a thermal IR ring-array imager 500 comprising a ring-shaped detector element 510 that is formed on a substrate 520. The ring-shaped detector element 510 comprises a first circular array of infrared detectors 512 and a second circular array of infrared detectors 514, wherein the first and second circular arrays 512 and 514 comprise a plurality of infrared detectors 512A and 514A, respectively.

The thermal IR ring-array imager 500 is similar to the thermal IR ring-array imager 400 of FIG. 7 in that the thermal IR ring-array imager 500 comprises two circular arrays of infrared detectors 512 and 514. However, in the embodiment of FIG. 8, the infrared detectors 512A and 514A of the ring-shaped detector element 510 are offset from each other by ½ of the area of the infrared detectors 512A and 514A. With this embodiment, the ½ spacing offset of the infrared detectors increases the imaging resolution by a factor of two (2), as compared to the embodiment of FIG. 7 where the infrared detectors 412A and 414A are fully aligned. Again, a ring-shaped focusing element can be implemented with the thermal IR ring-array imager 500 of FIG. 8 using similar techniques discussed above with reference to FIGS. 4, 5 and 6.

FIG. 9 is a schematic side view of a thermal IR ring-array imager according to another embodiment of the invention. In particular, FIG. 9 schematically depicts a thermal IR ring-array imager 600 comprising a ring-shaped detector element 610 that is formed on a substrate 620. The ring-shaped detector element 610 comprises a first circular array of infrared detectors 612, a second circular array of infrared detectors 614, and a third circular array of infrared detectors 616. The first, second and third circular arrays of infrared detectors 612, 614 and 616 comprise a plurality of infrared detectors 612A, 614A, and 616A, respectively.

In the embodiment of FIG. 9, the infrared detectors 612A, 614A, and 616A of the ring-shaped detector element 610 are offset from each other by ⅓ of the area of the infrared detectors 612A, 614A, and 616A. With this embodiment, the ⅓ spacing offset between the infrared detectors provides an increase in the imaging resolution by a factor of four (4), as compared to the embodiment of FIG. 7 where the infrared detectors 412A and 414A are fully aligned. Again, a ring-shaped focusing element can be implemented with the thermal IR ring-array imager 600 of FIG. 9 using similar techniques discussed above with reference to FIGS. 4, 5 and 6.

Figure 10:
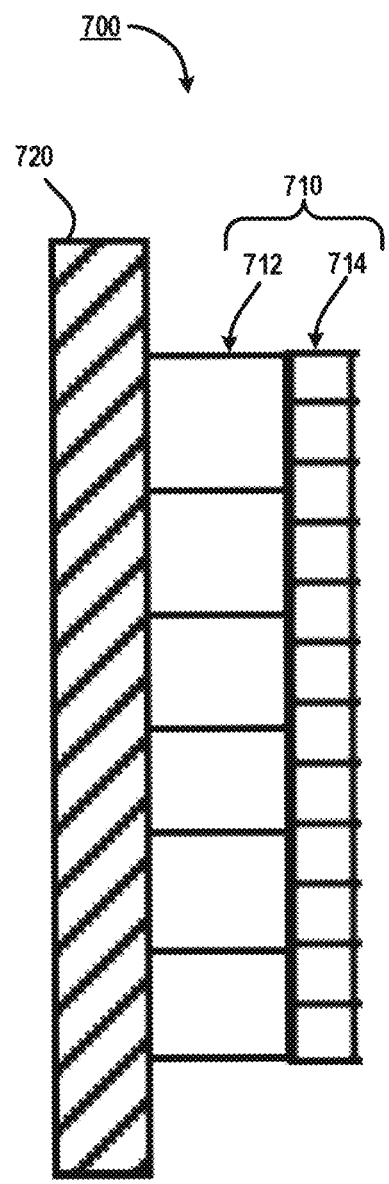
FIG. 10 is a schematic side view of a ring-array imager according to another embodiment of the invention.

FIG. 10 is a schematic side view of a ring-array imager according to another embodiment of the invention. In particular, FIG. 10 schematically depicts a ring-array imager 700 comprising a ring-shaped detector element 710 that is formed on a substrate 720. The ring-shaped detector element 710 comprises a circular array of infrared detectors 712 and a circular array of visible light detectors 714. In this embodiment, the circular array of visible light detectors 714 are configured to implement side-scan imaging (in the visible spectrum) in conjunction with the circular array of infrared detectors 712, to thereby capture and provide additional information (e.g., pill position, tissue surface information, etc.), which can be used to generate an overlay image or otherwise provide context for an acquired thermal image, using known techniques. Again, a ring-shaped focusing element can be implemented with the ring-array imager 700 of FIG. 10 using similar techniques discussed above with reference to FIGS. 4, 5 and 6.

Figure 11:
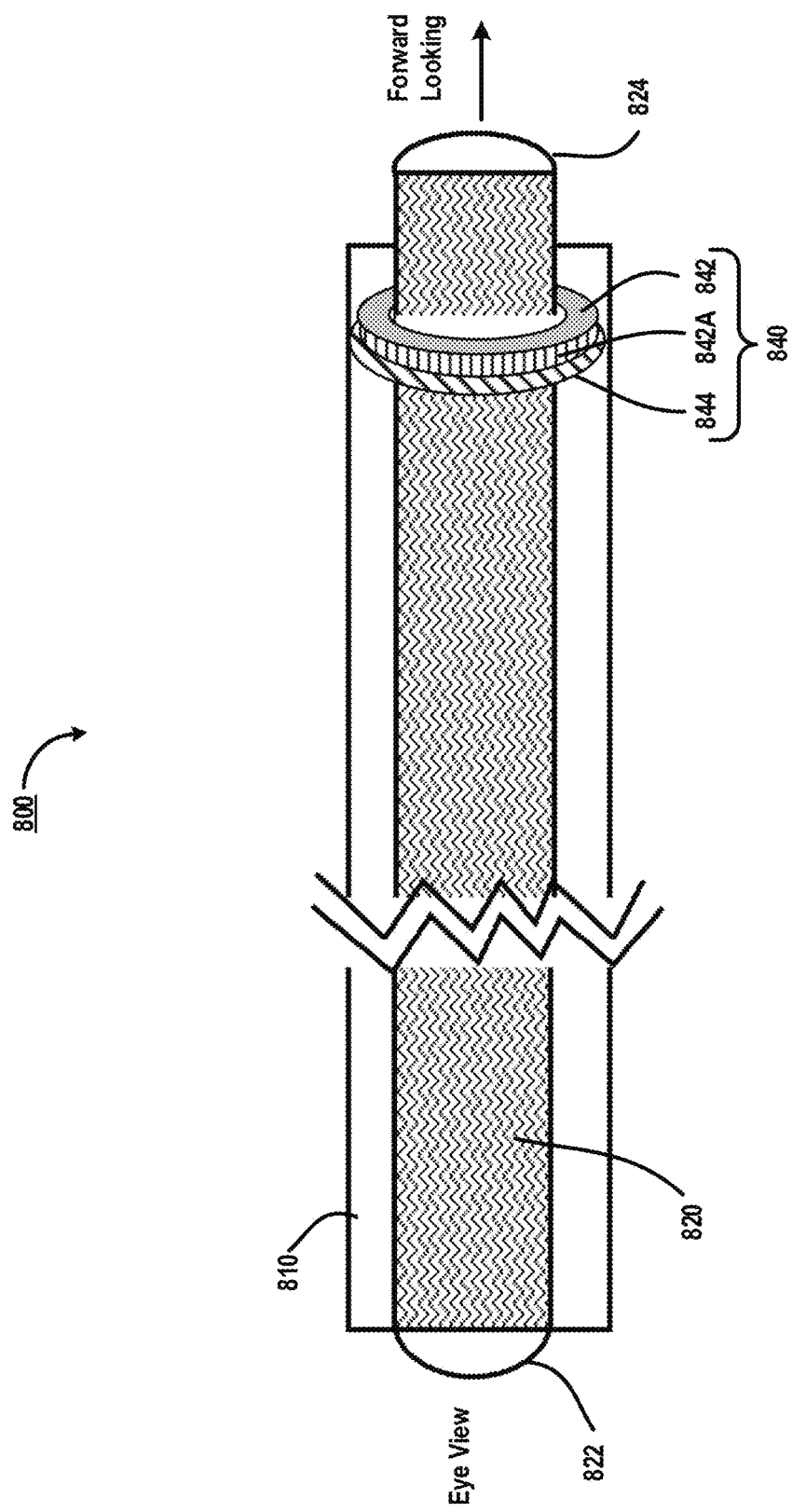
FIG. 11 schematically illustrates an endoscope device comprising an integrated thermal IR ring-array imager, according to an embodiment of the invention.

In other embodiments of the invention, a thermal IR ring-array imager can be implemented with an endoscope device to provide a real-time side-scanning video view. For example, FIG. 11 schematically illustrates an endoscope device comprising an integrated thermal IR ring-array imager device, according to an embodiment of the invention. In particular, FIG. 11 schematically illustrates an endoscope device 800 comprising a housing 810, a fiber optic bundle 820, and first and second viewing lenses 822 and 824 connected to the ends of the fiber optic bundle 820. The first lens 822 provides an eye view and the second lens 824 provides a real-time forward looking visible light view of anatomical objects being examined.

A thermal IR ring-array imaging device 840 is connected at a forward end of the endoscope 800. The thermal IR ring-array imaging device 840 comprises a ring-shaped detector element 842 that is formed on a substrate 844. The ring-shaped detector element 842 comprises a circular array of infrared detectors 842A formed around an outer perimeter surface of the ring-shaped detector element 842 to support thermal IR side-scan imaging as discussed herein. The fiber optic bundle 820 passes through an opening in the substrate 844 and passes through the interior of the ring-shaped detector element 842, whereby the thermal IR ring-array imaging device 840 is securely at the forward end of the endoscope 800. The detector circuitry (not shown) can be formed on the substrate 844. Electrical wiring and interconnections can extend through the housing 810 to provide power to the thermal IR ring-array imaging device 840 and transmit real time video of thermal IR images captured by the thermal IR ring-array imaging device 840. The embodiment of FIG. 11 allows a gastroenterologist to utilize an optical fiber endoscope for real-time visible light viewing while providing the added benefits of capturing real-time thermal IR video images concurrently with a real-time visible light view of an anatomical object being examined.

Figure 12:
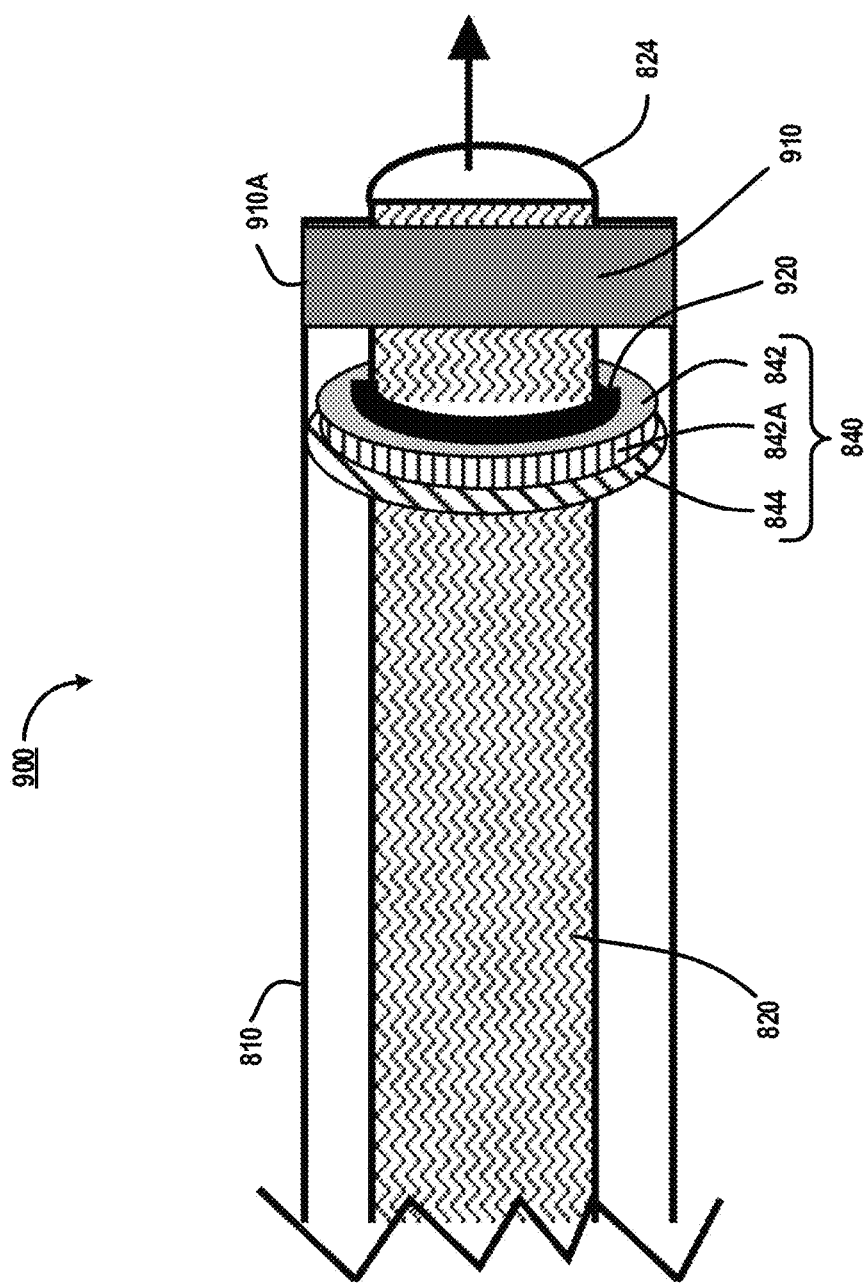
FIG. 12 schematically illustrates an endoscope device comprising an integrated thermal IR ring-array imager, according to another embodiment of the invention.

In another embodiment, thermal electric (TE) cooling can be implemented in conjunction with the endoscope device 800 of FIG. 12 to provide heating and cooling capabilities that enhance the acquisition of thermal images. For example, FIG. 12 schematically illustrates an endoscope device 900 according to another embodiment of the invention. The endoscope device 900 is similar to the endoscope device 800 discussed above with reference to FIG. 11, except that in the embodiment of FIG. 12, a thermal electric (TE) device 910 is placed at the forward end of the endoscope 900 for the purpose of heating and cooling tissue surrounding the forward end of the endoscope 900.

In particular, the TE device 910 can be operated using known techniques by reversing a bias voltage in the body of the TE device 910. This reverse in the bias voltage across the TE device 910 can make the outer surface region 910A of the TE device 910 hot when it is cold, and vice versa. The implementation of the TE device 910 provides an additional capability to heat and cool the surrounding tissue under examination, so that the overall system can yield different image results of a given region of tissue by controlling the surface temperature of the tissue above and below the ambient temperature of the tissue inside of the GI tract. For example, if the tissue can be artificially heated or cooled, one can study the heat soaking nature of the tissue to reveal tissue density and other target conditions of the tissue.

In another embodiment, the thermal IR ring-array imager 840 comprises a TE cooling ring 920 disposed on an inner surface region of the ring-shaped detector element 842. The TE cooling ring 920 can be controlled to cool down the ring-shaped detector element 842 and substrate 844 to increase the sensitivity of the infrared detectors for thermal IR imaging.

In yet another embodiment, a thermal transfer ring can be placed at the forward end of the endoscope 900 (in place of the TE device 910) wherein the thermal transfer ring is fabricated with internal piping that can be used to cool or heat the surrounding tissue at the forward end of the endoscope 900 by pumping hot or cold liquid through the piping using tubes that extend to the back end viewing section of the endoscope 900 to accommodate the transfer of heating or cooling liquids to the thermal transfer ring. In addition, a thermal transfer ring can be used in conjunction with the ring-shaped detector element 842 to cool the infrared detectors of the ring-shaped detector element 842.

Although embodiments of the invention have been described herein with reference to the accompanying drawings, it is to be understood that embodiments of the invention are not limited to the described embodiments, and that various changes and modifications may be made by one skilled in the art resulting in other embodiments of the invention within the scope of the following claims.

What is claimed is:

1. An imaging device, comprising:
a planar substrate comprising circuitry;
a ring-shaped detector element disposed on a surface of the planar substrate, the ring-shaped detector element comprising a circular array of infrared detectors configured to detect thermal infrared radiation, wherein the infrared detectors are disposed normal to the surface of the planar substrate and face in a radially outward direction from a center of the ring-shaped detector element, and wherein the ring-shaped detector element comprises interconnect structures to electrically connect the infrared detectors to the circuitry of the planar substrate; and
a ring-shaped focusing element concentrically disposed around the ring-shaped detector element and configured to direct focused incident infrared radiation towards the circular array of infrared detectors;
wherein the circuitry is configured to receive and process data generated by the infrared detectors to generate an image.

2. The imaging device of claim 1, wherein the ring-shaped focusing element comprises a plurality of pinholes configured to allow focused incident infrared energy to pass through the ring-shaped focusing element towards the infrared detectors.

3. The imaging device of claim 2, wherein each infrared detector is aligned to only one pinhole.

4. The imaging device of claim 2, wherein each infrared detector is aligned to two or more of the plurality of pinholes.

5. The imaging device of claim 1, wherein the imaging device is an ingestible imaging device.

6. The imaging device of claim 1, wherein the imaging device is an endoscope.

7. The imaging device of claim 1, wherein the circular array of infrared detectors comprises a first circular array of infrared detectors and a second circular array of infrared detectors disposed adjacent to the first circular array of infrared detectors.

8. The imaging device of claim 7, wherein the infrared detectors of the first circular array of infrared detectors are offset from the infrared detectors of the second circular array of infrared detectors.

9. The imaging device of claim 8, wherein the infrared detectors of the first circular array of infrared detectors are offset from the second circular array of infrared detectors by about ⅓ or about ½ of an area of the infrared detectors.

10. The imaging device of claim 1, further comprising a circular array of visible light detectors disposed adjacent to the circular array of infrared detectors.

* * * * *